United States Patent [19]

Gorvin

[11] 4,061,768
[45] Dec. 6, 1977

[54] CERTAIN CYCLIC CARBONYL COMPOUNDS USED IN THE PROPHYLAXIS OF ALLERGIC CONDITIONS

[75] Inventor: John Henry Gorvin, London, England

[73] Assignee: Burroughs Wellcome Co., N.C.

[21] Appl. No.: 642,662

[22] Filed: Dec. 19, 1975

Related U.S. Application Data

[60] Division of Ser. No. 338,578, March 6, 1973, Pat. No. 3,950,342, which is a continuation of Ser. No. 287,043, July 9, 1972, abandoned.

[30] Foreign Application Priority Data

| Feb. 24, 1972 | United Kingdom | 8609/72 |
| Feb. 24, 1972 | United Kingdom | 8610/72 |
| Aug. 29, 1972 | United Kingdom | 39940/72 |
| Aug. 29, 1972 | United Kingdom | 40079/72 |
| Sept. 8, 1971 | United Kingdom | 41852/71 |

[51] Int. Cl.$^2$ .................. A61K 31/35; C07D 311/00
[52] U.S. Cl. .................. 424/283; 260/257; 260/335; 424/257
[58] Field of Search .................. 424/283; 260/335

[56] References Cited

U.S. PATENT DOCUMENTS

| 3,706,768 | 12/1972 | Bays | 260/335 |
| 3,818,042 | 6/1974 | Pfister et al. | 260/335 |
| 3,859,286 | 1/1975 | Fleming et al. | 260/247.5 R |
| 3,859,307 | 1/1975 | Carr et al. | 260/335 |
| 3,886,181 | 5/1975 | Pfister et al. | 260/335 |
| 3,950,342 | 4/1976 | Gorvin | 260/335 X |
| 3,959,482 | 5/1976 | Hodson et al. | 424/304 |

Primary Examiner—Leonard Schenkman
Attorney, Agent, or Firm—Donald Brown

[57] ABSTRACT

A pharmaceutical composition and method for inhibiting the symptoms of allergic conditions such as asthma or allergic rhinitis which comprises administering a compound of the formula

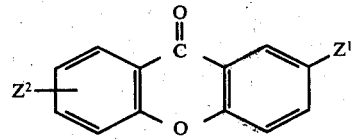

where $Z^2$ is in the 6 position, wherein $Z^1$ and $Z^2$ are carboxylate, a pharmaceutically acceptable carboxylate salt, alkyl carboxylate, carboxamide, N-alkyl carboxamide, or N,N,-dialkylcarboxamide where alkyl in the above has 1 to 6 carbon atoms.

24 Claims, No Drawings

CERTAIN CYCLIC CARBONYL COMPOUNDS USED IN THE PROPHYLAXIS OF ALLERGIC CONDITIONS

This is a division of U.S. patent application Ser. No. 338,578 filed Mar. 6, 1973, now U.S. Pat. No. 3,950,342 dated Apr. 13, 1976, which is a continuation of U.S. patent application Ser. No. 287,043 filed July 9, 1972, now abandoned.

Certain acridone and xanthone compounds, each of which is 2-substituted by a carboxyl group or a salt, ester or optionally substituted amide thereof and each of which is optionally substituted in the 5-,6-,7- or 8- position, by a second carboxyl group, salt, ester or optionally substituted amide thereof, the substituent in the 5-,6-,7- or 8- position of the acridone compounds, also being selected from cyano, halogen, nitro, alkyl, alkoxy and acyl, are useful for the relief or prophylaxis of allergic conditions.

The invention relates to tricyclic compounds having medicinal properties, the synthesis of the compounds and their adaptation for medicinal use.

It has been found that tricyclic compounds of formula I defined hereinbelow are active in mammals and in in vitro mammalian preparations as inhibitors or allergic reactions associated with reaginic antibodies of the kind responsible for asthma in man, and that this effect is attributable to the suppression of the release of anaphylactic mediators.

In formula I

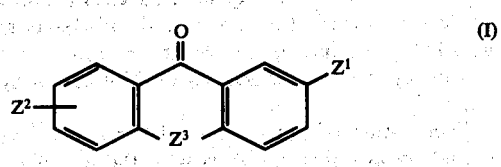

$Z^1$ is a carboxyl group, a carboxylate salt group, an alkyl carboxylate group wherein the alkyl moiety has 1 to 6, preferably 1 to 4 carbon atoms or a carboxamide group optionally N-substituted by alkyl having 1 to 6, preferably 1 to 4 carbon atoms; $Z^3$ represents an oxygen atom or a group $NR^1$ in which $R^1$ is a hydrogen atom or an alkyl group having 1 to 4 carbon atoms; and $Z^2$ is a substituent and has the same meaning as $Z^1$ or is a hydrogen atom or when $Z^3$ is a group $NR^1$ as defined above, $Z^2$ is a nitro group, a cyano group, a halogen atom preferably chlorine or bromine, an acyl group, an alkyl group or an alkoxy group wherein the "alkyl" moiety of each of the acyl, alkyl and alkoxy groups has 1 to 6 carbon atoms.

Especially active compounds of formula I are Xanthone-2,6-dicarboxylic acid and pharmaceutically acceptable salts thereof, especially the disodium, dipotassium and diammonium salts.

Highly active compounds of formula A include:
Acridone-2,6-dicarboxylic acid; and
pharmaceutically acceptable salts thereof.
Moderately active compounds of formula I include:
N-methylacridone-2,7-dicarboxylic acid;
Xanthone-2,7-dicarboxylic acid;
Acridone-2-carboxylic acid;
Xanthone-2-carboxylic acid; and
Pharmaceutically acceptable salts thereof.

The inhibition activity of the compounds of formula I has been demonstrated (a) in tests using the response of passive cutaneous anaphylaxis (PCA test) in which is measured the skin reaction produced as the result of interaction between specific antigen injected intravenously and cell-fixed reaginic antibody previously injected into the skin of a mammal (see for example Z. Ovary: Fedn. Proc. Am. Soc. exp. Biol. 24, 94 (1965)), (b) by measurement of the amount of histamine released after antigen challenge of peritoneal mast cells from actively sensitised rats (see for example, 1. Acta Pharmacol. et Toxicol 30, supp. 1 (1971), 2. Thorax, 27/1, 38 (1972), and (c), by measurement of the histamine released from human chopped lung tissue passively sensitised in vitro with reaginic antibody when challenged with the homologous antigen (Br. Med. J. 3,272 (1968)). The activity of acids of formula I has been demonstrated as described hereinabove using solutions of the carboxylate anion.

For the sake of convenience, compounds of formula I wherein either of $Z^1$ and $Z^2$ is or both are an alkyl carboxylate group, shall hereinafter be referred to as 'esters' of formula I. Similarly references to 'amides' of formula I shall be construed as references to compounds of formula I wherein one or both of $Z^1$ and $Z^2$ is an optionally substituted carboxamide, and references to 'salts' of formula I shall mean compounds of formula I wherein one or both of $Z^1$ and $Z^2$ is a carboxylate salt group.

Pharmaceutically acceptable salts of formula I include ammonium salts, alkali metal salts such as sodium and potassium salts, alkaline earth salts such as magnesium and calcium salts, and salts of organic bases, for example, amine salts such as triethanolamine and diethylaminoethylamine salts, and piperazine and morpholine salts. Especially valuable are water soluble salts of formula I most preferably those having a solubility in water of at least 1 mg/ml.

The anti-allergic activity of the salts of formula I lies in the anion and the nature of the cation does not contribute to the activity, but for medicinal purposes the cation must of course be pharmaceutically acceptable.

Suitable substituted carboxamide groups include N-alkyl and N,N-dialkyl substituted carboxamide groups wherein the alkyl moiety is an alkyl group having 1 to 6 carbon atoms, preferably 1 to 4 carbon atoms.

Xanthone compounds of the present invention include tricyclic compounds of formula

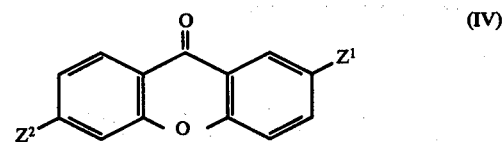

wherein $Z^1$ and $Z^2$ are the same or different and each is selected from a carboxyl group, carboxylate salt group, an alkyl carboxylate group having 1 to 6 carbon atoms in the alkyl moiety and a carboxamide group optionally N-substituted by an alkyl group having 1 to 6 carbon atoms.

Novel compounds of the present invention include tricyclic compounds of the formula

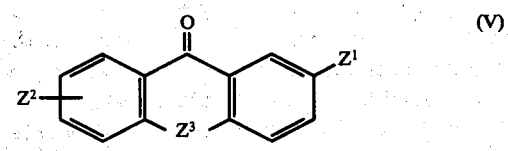

wherein $Z^1$ is a carboxyl group, a carboxylate salt group, an alkyl carboxylate group having 1 to 6 carbon atoms in the alkyl moiety, or a carboxamide group optionally N-substituted by alkyl having 1 to 6 carbon atoms; $Z^3$ is oxygen or a group $NR^1$ where $R^1$ is a hydrogen atom or an alkyl group having 1 to 4 carbon atom and $Z^2$ is a carboxyl group, a carboxylate salt group, an alkyl carboxylate group having 1 to 6 carbon atoms in the alkyl moiety or is a carboxamide optionally N-substituted by alkyl having 1 to 6 carbon atoms or when $Z^3$ is a group $NR^1$ as defined hereinabove $Z^2$ is a halogen atom, cyano group, nitro group, alkyl group, acyl group or alkoxy group wherein the alkyl moiety of each of the alkyl, acyl and alkoxy groups has 1 to 6 carbon atoms, provided that when $Z^3$ is an oxygen atom $Z^2$ is not a 7-carboxyl group, 7-carboxylate salt, 7-alkyl carboxylate or 7-carboxamide optionally N-substituted by alkyl.

Novel acridone and N-alkyl acridone compounds of the present invention include tricyclic compounds of the formula

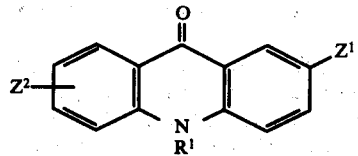 (VII)

wherein $R^1$ is a hydrogen atom or an alkyl group having 1 to 4 carbon atoms, $Z^1$ is a carboxyl group, a carboxylate salt group, an alkyl carboxylate group having 1 to 6 carbon atoms in the alkyl moiety, or a carboxamide group optionally N-substituted by alkyl having 1 to 6 carbon atoms and $Z^2$ is hydrogen or a substituent and has the same meaning as $Z^1$ or is a nitro group, a cyano group, a halogen atom, an acyl group, an alkyl group, or an alkoxy group wherein the alkyl moiety of each of the acyl, alkyl and alkoxy groups is an alkyl group has 1 to 6 carbon atoms provided that $R^1$ and $Z^2$ are not both hydrogen.

Novel acridone compounds of the present invention include compounds of formula

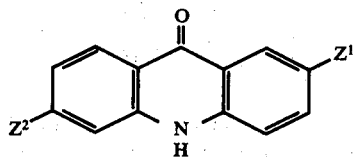 (VIII)

wherein $Z^1$ is a carboxyl group, a carboxylate salt group, an alkyl carboxylate group having 1 to 6 carbon atoms in the alkyl moiety, or a carboxamide group optionally N-substituted by alkyl having 1 to 6 carbon atoms and $Z^2$ has the same meaning as $Z^1$ or is a nitro group, a cyano group, a halogen atom, an acyl group, an alkyl group or an alkoxy group wherein the 'alkyl' moiety of each of the acyl, alkyl and alkoxy groups is an alkyl group having 1 to 6 carbon atoms.

Novel xanthone compounds of the present invention include tricyclic compounds of formula

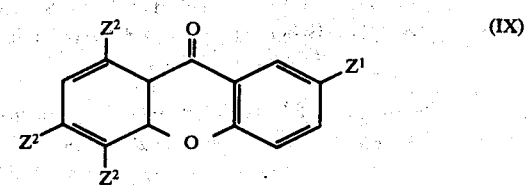 (IX)

wherein $Z^1$ is a substituent carboxyl group, carboxylate salt group, alkyl carboxylate having 1 to 6 carbon atoms in the alkyl moiety or carboxamide optionally N-substituted by alkyl having 1 to 6 carbon atoms and each $Z^2$ group is a hydrogen atom or has the same meaning as $Z^1$ provided that only one of the $Z^2$ groups is a substituent group as defined above.

Novel compounds of the present invention also include solid tricyclic compounds of formula

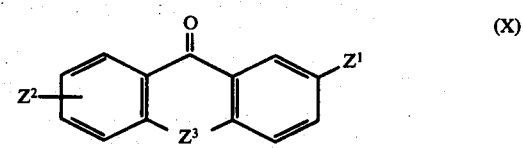 (X)

wherein $Z^2$ is a carboxylate salt group, $Z^3$ is an oxygen atom, or a group $NR^1$ wherein $R^1$ is a hydrogen atom or an alkyl group having 1 to 4 carbon atoms, and $Z^2$ has the same meaning as $Z^1$ provided that when $Z^3$ is a group $NR^1$ as defined hereinabove, $Z^2$ is also selected from a cyano group, a halogen atom, a nitro group, an alkyl group, an acyl group and an alkoxy group wherein the 'alkyl' moiety of the alkyl, acyl and alkoxy groups is an alkyl group having 1 to 6 carbon atoms; or when $Z^3$ is a group $NR^1$ as defined above $Z^2$ is also a hydrogen atom.

Preparation of compounds of formula I may be effected by any method known in the art of preparing them and compounds of analogous chemical structure. In general the compounds of formula I wherein one or both of $Z^1$ and $Z^2$ is a carboxylate derivative (for example an amide, ester or salt), are prepared by suitable treatment of the corresponding acid. However, in certain circumstances it is possible to prepare such derivatives without prior isolation of the carboxylic acid, either by the choice of suitable reactants or by forming the desired derivative in a reaction mixture or the acid, without first isolating the acid.

Methods for the preparation of dicarboxylate acids and salts of formula are described hereinbelow, but it will be understood that in some instances the methods may be adopted to yield the corresponding esters or amides of formula I 1. Hydrolysis of a compound of formula XI

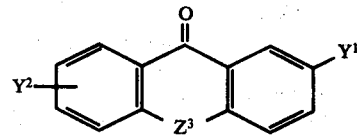 (XI)

wherein $Y^1$ is a carboxyl group precursor, such as a nitrile group, trichloromethyl group or a group $COL^1$ wherein $L^1$ is a leaving group, such as a nucleophilic atom or group, for example, a trichloromethyl group, an optionally substituted amino group, a halogen atom or an alkoxy group; $Y^2$ is a carboxyl group or a group $Y^1$ precursor as defined above; and $Z^3$ has the meaning defined in formula I. Hydrolysis is conveniently effected by heating a compound of formula XI with a dilute aqueous alkali, or with a dilute aqueous mineral acid optionally with an organic acid. For example, one may use dilute sulpuric acid, dilute hydrochloric acid with acetic acid, or dilute aqueous sodium hydroxide solution. Hydrolysis with aqueous alkali will yield inter alia an aqueous solution of a dicarboxylate salt but if it is desired to collect the maximum amount of dicarboxylic acid, then the reaction mixture should be acidified when hydrolysis is completed to precipitate the acid. On the other hand if the desired end-product is the dicarboxylate salt, then following hydrolysis, the cation of the desired salt may be added to precipitate the desired salt by the common ion effect without prior isolation of the corresponding acid.

By means of nucleophilic substitution reactions analogous to hydrolysis, for example, alcoholysis and ammonolysis, compounds of formula I other than the dicarboxylic acid may be prepared directly from compounds of formula XI. Thus reaction of a compound of formula XI with an appropriate alcohol yields an ester of formula I, and reaction with ammonia or an appropriate primary or secondary amine yields an amide of formula I.

2. Cyclisation of a compound of formula XII

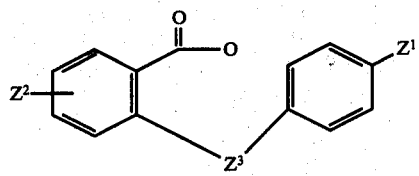

(XII)

wherein $Z^1$, $Z^2$ and $Z^3$ have the meaning defined in formula I and Q is a hydroxyl, alkoxy or an optionally substituted amino group, a halogen atom, or a $RCO_2$ group, a $ROCO_2$ group or a $RSO_3$ group wherein R is alkyl or aryl. Cyclisation may be effected by heating a compound of formula XII at an elevated temperature, for example up to about 300° C. Preferably heating is carried out in the presence of a Lewis acid under anhydrous conditions or a protonic acid, optionally in the presence of a non-polar solvent. Preferred Lewis acids include boron trifluoride and aluminium trichloride and preferred protonic acids include sulphuric, hydrochloric and polyphosphoric acids.

If, however, $Z^2$ is a carboxylate substituent in the 5-position of the nascent compound of formula I, reaction conditions and/or the group Q must be chosen so as to avoid reaction of the group $Z^2$.

The intermediate compounds of formula XIII

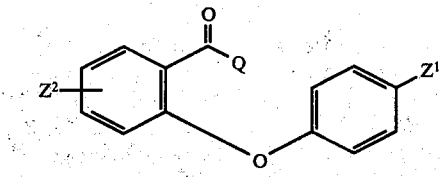

(XIII)

may be prepared by the reaction of a suitable monohydric phenol compound of formula XIV

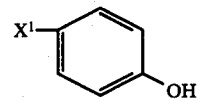

(XIV)

wherein $X^1$ is a nitrile or a carbalkoxy group, with a suitable activated mono-nitrophenyl compound of formula XV

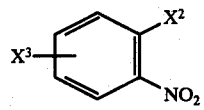

(XV)

wherein $X^2$ and $X^3$ are each a nitrile or carbalkoxy group, so as to produce a diphenyl ether of formula XVI

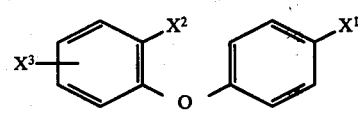

(XVI)

wherein $X^1$, $X^2$ and $X^3$ have the same meaning as above. The reaction is effected in a dipolar aprotic soluent such as dimethyl sulfoxide, dimethyl acetamide, N-methyl-2-pyrrolidone, sulfolane, hexamethylphosphoramide, dimethyl formamide and acetonitrile, at an elevated temperature of from 50° to 150° C preferably from 100° to 120° C. In the case of compounds of formula XVI wherein the groups $X^1$ and $X^3$ are the same as groups $Z^1$ and $Z^2$ as previously defined and wherein the group $X^2$ is the same as the group C(:O)Q as defined in formula XIII no further reaction prior to cyclisation is required. In the case of other compounds of formula XVI, for example, those wherein one or more of the group $X^1$, $X^2$ and $X^3$ is a nitrile group, the said other compounds are hydrolysed so as to yield a compound of formula XIII wherein Q is a hydroxyl group or an amino group. Hydrolysis is conveniently effected by heating a compound of formula XVI with dilute aqueous mineral acid optionally in the presence of an organic acid, or with dilute aqueous alkali.

3. Oxidation of a compound of formula XVII

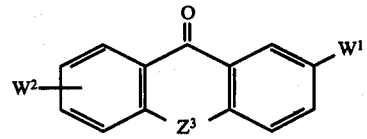

(XVII)

wherein $W^1$ and $W^2$ are each a lower alkyl group or a group C(:O)R wherein R is an optionally substituted lower alkyl group having 1 to 4 carbon atoms, or is OH, provided that $W^1$ and $W^2$ are not both C(:O)OH and $Z^3$ has the meaning defined in formula I. Oxidation of compounds wherein $W^1$ and/or $W^2$ are lower alkyl groups may be effected with such conventional oxidising agents as acid or alkaline aqueous potassium permanganate solution; chromium trioxide, for example, with acetic acid or sulphuric acid; oxygen in the presence of a conventional catalyst such as lead, cobalt and manganese salts, for example, lead acetate; or aqueous solutions of sodium dichromate.

Oxidation of compounds wherein $W^1$ and/or $W^2$ are the groups C(:O)R may be effected with such conventional oxidising agents as chromium trioxide, for example, with acetic acid or sulphuric acid; aqueous solution of salts of hypochlorous and hypobromous acids in the presence of a base; sodium or possium dichromate with acetic acid; or nitric acid. These oxidation procedures are advantageously effected with heating in the liquid phase.

4. Oxidation of a compound of formula XVIII

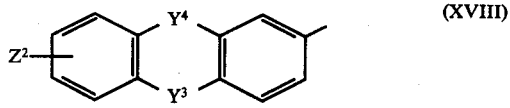   (XVIII)

Wherein $Z^1$ and $Z^2$ have the meaning defined hereinbefore in formula I, $Y^3$ is a group $Z^3$ as defined hereinbefore in formula I and $Y^4$ is a methylene group; or $Y^4$ is selected from CH and CR wherein R is lower alkyl, and $Y^3$ is N. Oxidation of compounds of formula XVIII may be effected with such conventional oxidising agents as nitric acid; aquous solutions of hypochlorous and hypobromous acids in the presence of base; chromium trioxide, for example with acetic acid or with sulphuric acid; or aqueous solutions of sodium dichromate.

Oxidation of compounds of formula XVIII wherein $Y^4$ is a methylene group and $Y^3$ is oxygen or NR wherein R is alkyl having 1 to 4 carbon atoms, may also be effected with such conventional oxidising agents as oxygen in the presence of triton B in pyridine solution; or oxygen in the presence of potassium t-butoxide in the presence of t-butanol and dimethylsulphoxide.

Compounds analogous to the compounds of formula XVIII wherein either or both of $Z^1$ and $Z^2$ is replaced by a group $W^1$ or $W^2$ as defined in formula XVII, may also be oxidised so as to produce dicarboxylate acids or salts of formula I. Oxidation in the case of such compounds may be effected with such conventional oxidising agents as chromium trioxide, for example, with acetic acid or with sulphuric acid, or aqueous solutions of sodium dichromate. In the case of such compounds wherein neither $W^1$ or $W^2$ is alkyl, oxidation may also be effected with such conventional oxidising agents as aqueous solutions of salts of hypobromous or hypochlorous acids in the presence of a base; or nitric acid. Advantageously any of the hereinbefore described oxidation procedures wherein aquous solutions of sodium dichromate are employed, are carried out at an elevated temperature in a sealed container. Oxidation of the groups $W^1$ and $W^2$ in such case is preferably effected at a temperature of from 200° to 210° C. Oxidation of the xanthone nucleus in such a case is preferably effected at a temperature of from 240° to 260° C.

5. Cyclisation of a compound of formula XIX

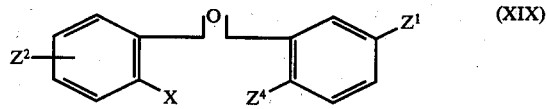   (XIX)

wherein $Z^1$ and $Z^2$ have the meaning defined hereinbefore in formula I and $Z^4$ is a hydroxyl group or a group $NHR^1$ wherein $R^1$ is hydrogen or alkyl having 1 to 4 carbon atoms and X is a leaving group, for example, a halogen for example chlorine; hydroxyl; p-toluenesulphonyloxy; nitro; or sulphinate. Cyclisation may be effected by heating a compound of formula XIX wherein X is other than nitro at an elevated temperature up to about 120° C, in the presence of an alkaline hydroxide such as sodium hydroxide and optionally in the presence of a polar solvent such as water or aqueous ethanol. Where X is a nitro group cyclisation may be advantageously effected in a dipolar aprotic soluent such as dimethyl sulfoxide, dimethyl acetamide, N-methyl-2-pyrrolidone sulfolane, hexamethylphosphoramide, dimethyl formamide and acetonitrile, at an elevated temperature of from 50° to 150° C preferably from 100° to 120° C.

Alternatively a compound of formula XIX wherein one or both of $Z^1$ and $X^2$, is or are, replaced by a carboxyl group precursor $Y^1$ as defined hereinbefore, and X is other than nitro, may be simultaneously cyclised and hydrolysed. Such a reaction may be effected by heating such a compound of formula XIX at an elevated temperature, up to about 120° C, in the presence of an alkaline hydroxide such as sodium hydroxide and optionally in the presence of a polar solvent such as water or aqueous ethanol.

The intermediate compounds of formula XIX may be prepared by a Friedel Crafts reaction between a compound of formula XX

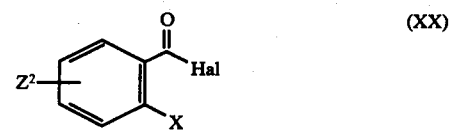   (XX)

wherein Hal is a halogen atom and X and $Z^2$ have the meaning given in formulae XIX and I respectively, with a compound of formula XXI

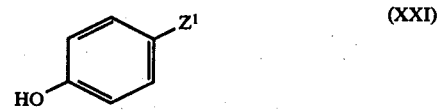   (XXI)

wherein $Z^1$ has the same meaning as in formula XIX. The reaction is effected in the presence of a Lewis acid such as aluminum chloride, optionally in the presence of a polar solvent such as nitrobenzene at an elevated temperature, preferably from 50° C up to the reflux temperature of the reaction mixture.

Alternatively the intermediate compounds of formula XIX wherein $Z^4$ is a hydroxyl group may be prepared by heating the appropriate compound of formula XXII

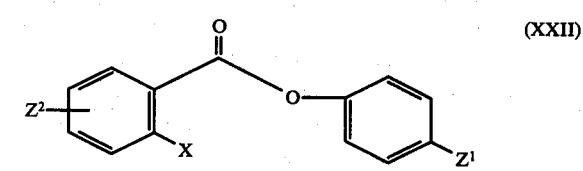   (XXII)

wherein $Z^1$, $Z^2$ and X are as defined in formula XIX, in the presence of a Lewis acid such as aluminum chloride, optionally in the presence of a non-polar soluent such as nitrobenzene or tetrachloroethane, at an elevated temperature from 50° up to the reflux temperature of the reaction mixture. Under such conditions compounds of formula XXII rearrange to the corresponding compounds of formula XIX.

The method described hereinbefore for the preparation of dicarboxylate compounds of formula I may also be used to synthesize the corresponding 2-monocarboxylate compounds of formula I and the $Z^2$ substituted 2-monocarboxylate compounds of formula I wherein the $Z^2$ substituent is a nitro group, a cyano group, a halogen atom, an acyl group, an alkyl group or an alkoxy group as defined in formula I, provided the reaction conditions are chosen in the case of oxidation methods to preferably minimise complete oxidation when $Z^2$ is alkyl or acyl so as to retain the $Z^2$ substituent, or in the case of hydrolysis methods to avoid complete hydrolysis when $Z^2$ is cyano so as to retain the $Z^2$ substituent.

N-alkyl acridone esters of formula I may also be prepared by alkylation of corresponding acridone compounds of formula I. Alkylation may be effected by any conventional process for alkylation of secondary amino groups, for example, by reaction with a group $RX^5$ wherein R is alkyl having 1 to 6 carbon atoms and $X^5$ is a leaving group such as a halogen atom, in the presence of a strong base. Suitable bases are sodamide and sodium hydride. Desirably alkylation is effected in the presence of a solvent which includes dimethyl sulphoxide xylene, or liquid ammonia.

Pharmaceutically acceptable salts of acids of formula I are prepared by any conventional method, for example by neutralising the corresponding carboxylic acid with an appropriate Bonsted base, or by double decomposition of a salt of an acid of formula I so as to produce the desired salt of an appropriate pharmaceutically acceptable cation. The carboxylic acid may be either the isolated acid, or may be present in solution in the reaction mixture resulting from a preparation of the acid, for example by such a method as described hereinbefore. Suitable Bronsted bases include organic bases such as ethanolamine, and bases containing ammonium, and alkali metal and alkaline earth metal cations. Double decomposition may be effected advantageously in an ion exchange resin wherein a solution of a salt of an acid of formula I is passed through a cation exchange resin, the resin being charged with a pharmaceutically acceptable cation of the suitable base. Double decomposition may also be effected in ordinary solution between a salt of an acid of formula I and a salt of the desired pharmaceutically acceptable cation.

Specifically, pharmaceutically acceptable salts of Formula I may be prepared by one or more of the following methods.

1. Reaction in a polar medium of a compound of formula XXIII.

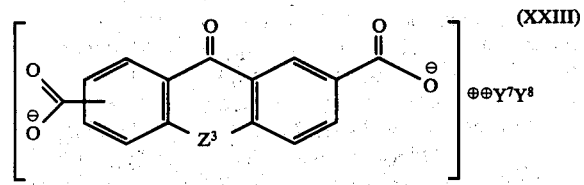

(XXIII)

wherein one of $Y^7$ and $Y^8$ is the hydrogen ion and the other represents the hydrogen ion or a cation of the desired salt, with a base of the desired salt, or when $Y^7$ and $Y^8$ represent together or separately a single or two cations other than the cation of the desired salt, and $Z^3$ has the meaning in formula I.

2. Reaction in a polar medium of a compound of formula XXIV

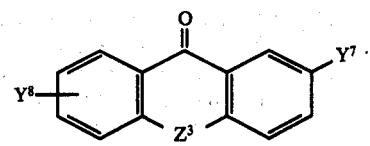

(XXIV)

wherein $Y^7$ and Y are the same or different and each is selected from a carboxylic group and a group $Y^1$ as defined hereinbefore in formula XI, and $Z^3$ has the same meaning as before, with an appropriate Bronsted base and, when the Bronsted base does not contain a hydroxyl ion, in the presence of water. Examples of appropriate Bronsted bases are alkali and alkaline earth metal oxides and hydroxides for producing corresponding alkali and alkaline earth metal salts of formula I. Preferably the reaction is effected with heating.

Salts of formula I may be isolated from a reaction medium by any conventional process for the isolation of salts from a solution thereof in a polar medium. Thus the salts may be isolated by precipitation of the salt or by removal of the polar medium.

Precipitation of the salt may be effected by mixed solvent crystallisation or by the addition of excess base or salt thereof so as to produce a concentration of the cation of the salt to be isolated, substantially in excess of the molar ratio thereof in said salt to be isolated.

Mixed solvent crystallisation may be effected by addition, to a solution of a salt of formula I in a polar medium, of a second polar solvent other than, but miscible with, the polar solvent already present and in which second solvent the salt of formula I is less soluble than in the polar solvent already present.

Removal of the polar medium may be effected by evaporation, for example, by freeze-drying, or by azeotropic distillation.

Desirably the salts of formula I were purified prior to incorporation in a pharmaceutical composition. Purification may be effected by any conventional method. A particularly valuable purification process comprises isolation of a crude solid salt of formula I from a reaction mixture wherein said salt has been produced, by any method for the isolation of salts of formula I as described hereinabove; dissolution of the salt in hydrochloric acid; recovery of the corresponding acid of formula I as a solid; neutralisation of the acid of formula I with a Bronsted base of which base the cation is the cation of the required salt of formula I; removal of solid impurities by filtration; and isolation of the salt of formula I by a method as described hereinabove.

Conveniently an acid of formula I may be purified prior to neutralisation, by recrystallisation or by isolation of a N,N-dimethylformamide adduct and subsequently heating the adduct to drive off the N,N-dimethylformamide.

Esters and amides of acids of formula I may be prepared by any conventional method including esterification of the acid or acid chloride with an alkyl alcohol to yield the corresponding alkyl ester, and reaction of the acid or acid chloride with ammonia or an alkylamine to yield the corresponding amide or N-alkyl substituted amide respectively. Compounds of formula I where $Z^1$ and $Z^2$ are different and are chosen from acid, ester, amide and salt functions, may be prepared by the above methods, and by partial hydrolysis where appropriate.

The compounds of formula I are useful in the treatment of prophylaxis of mammalian allergic conditions such as asthma and other allergic chest conditions, hay fever (allergic rhinitis), conjunctivitis, urticaria and eczema. In particular they are of value in reaginic antibody mediated Type I hypersensitivity asthma ('extrinsic asthma') and the socalled 'intrinsic asthma' in which no sensitivity to extrinsic antigen can be shown.

The magnitude of a prophylactic or therapeutic dose of a compound of formula I will of course vary with the nature and the severity of the allergic condition to be treated and with the particular compound of formula I and its route of administration. In general the dose range lies within the range of 2μg. to 100mg. per kg. body weight of a mammal.

In the case of an allergic condition as defined hereinbefore, for example, asthma, a suitable dosage is from 5 μg. to 0.5 mg., preferably from 20 μg. to 0.2 mg., for example about 0.1 mg., of a compound of formula I, per kg. of bodyweight of the patient undergoing treatment, when pulmonary administration as described hereinafter is employed. In the case where a composition for intravenous administration is employed a suitable dosage range is from 0.2 to 100 mg. of a compound of formula I per kg. of bodyweight of patient, and in the case where an oral composition is employed a suitable dosage range is from 2 to 50 mg. of a compound of formula I per kg. of bodyweight of a patient.

In the case where a composition for nasal administration is employed, for example, in the treatment of allergic rhinitis, a suitable dose is from 2 μg. to 4 mg. of a compound of formula I per kg. of bodyweight of patient.

In the case of xanthone-2, 6-dicarboxylate salts, particularly suitable dosages for the treatment of allergic asthma have been found to be as follows, all doses being given on the basis of the weight of the free dicarboxylic acid and as amounts per kg. of bodyweight of the patient undergoing treatment: for allergic asthma by pulmonary administration 30 μg to 0.3 mg. perferably 0.2 mg., by intravenous administration 2 to 15 mg. and by oral administration 15 to 60 mg.; and for allergic rhinitis by nasal administration 15 μg to 0.6 mg.

The pharmaceutical compositions of the present invention comprise a compound of formula I as an active ingredient, and may also contain a pharmaceutically acceptable carrier and optionally other therapeutic ingredients. The compositions include compositions suitable for oral, rectal, opthalmic, pulmonary, nasal, dermal, topical, or parenteral (including subcutaneous, intramuscular and intravenous) administration, although the most suitable route in any given case will depend on the nature and severity of the condition being treated, and on the nature of the active ingredient. They may be conveniently presented in unit dosage form and prepared by any of the methods well known in the art of pharmacy.

Pharmaceutical compositions of the present invention suitable for oral administration may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more accessory ingredients. In general the compositions are prepared by uniformly and intimately admixing the active ingredient with liquid carriers or finely divided solid carriers or both, and then, if necessary, shaping the product into the desired presentation. For example a tablet may be prepared by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from 200mg. to 500mg. of the active ingredient, and each cachet or capsule contains from 500 to 2000mg. of the active ingredient.

A particularly valuable form of a pharmaceutical composition of the present invention, for use in the treatment of allergic asthma, is a composition suitable for pulmonary administration via the buccal cavity; although of course conditions other than allergic asthma may also be treated by pulmonary administration of the composition.

Preferably the composition is such that particles having a diameter of 0.5 to 7μ most preferably 1 to 6μ, containing active ingredient, are delivered into lungs of a patient. This ensures that a maximal amount of active ingredient is administered to the alveolar sacs of the lungs and retained therein thus producing a maximal effect in the patient. Such compositions are most preferably in the form of dry powders for administration from a powder inhalation device or self-propelling powder-dispensing compositions.

Most preferably the powders of the pulmonary compositions as described hereinabove and hereinbelow comprise particles containing active ingredient of which particles at least 98% by weight have a diameter greater than 0.5μ and at least 95% by number have a diameter less than 7μ. Most desirably at least 95% by weight of the particles have a diameter greater than 1μ and at least 90% by number of the particles have a diameter less than 6μ.

The compositions in the form of dry powders preferably comprise particles containing the solid active ingredient, the particles having a diameter of 0.5 to 7μ most preferably 1 to 6μ. Preferably these compositions include a solid diluent in the form of a fine powder. These compositions may be conveniently presented in a pierceable capsule of a pharmaceutically acceptable material, for example gelatin. Such compositions may be conveniently prepared by comminution of solid active ingredient optionally with a solid diluent. If desired the resulting powder may be filled into a pierceable capsule of a pharmaceutically acceptable material.

Other valuable forms of a composition of the present invention that are suitable for pulmonary administration are self-propelling compositions. These self-propelling compositions may be either powder-dispensing compositions or compositions dispensing the active ingredient in the form of droplets of a solution or suspension.

Self-propelling powder-dispensing compositions preferably comprise dispersed particles of solid active ingredient, having a diameter of 0.5 to 7μ most preferably 1 to 6μ and a liquid propellant having a boiling point of below 65° F at atmospheric pressure. The liquid propellant may be any propellant known to be suitable for medicinal administration and may comprise one or more lower alkyl hydrocarbons, or halogenated lower alkyl hydrocarbons, or mixtures thereof. Chlorinated and fluorinated lower alkyl hydrocarbons are especially preferred as propellant. Generally the propellant may constitute 50 to 99.9% w/w of the composition whilst the active ingredient may constitute 0.1 to 20% w/w, for example, about 2% w/w, of the composition.

The pharmaceutically acceptable carrier in such self-propelling compositions may include other constituents in addition to the propellant, in particular a surfactant or a solid diluent or both. Surfactants are desirable in preventing agglomeration of the particles of active ingredient and in maintaining the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic Chemists Vol. 1 pp. 311–326 (1949)) of below 10, in particular esters and partial esters of fatty acids with aliphatic polyhydric alcohols, for instance, sorbitan monooleate and sorbitan trioleate, known commercially as 'Span 80' (Trade Name) and "Span 85" (Trade surfactants include alkali metal, ammonium and amine salts of dialkyl sulphosuccinate, where the alkyl groups have 4 to 12 carbon atoms, and alkylbenzene sulphonic acid where the alkyl group has 8 to 14 carbon atoms. The solid anionic surfactants may constitute up to 20% w/w of the composition, though preferably below 1% w/w of the composition.

Solid diluents may be advantageously incorporated in such self-propelling compositions where the density of the active ingredient differs substantially from the density of the propellant; also in order to help to maintain the active ingredient in suspension. The solid diluent is in the form of a fine powder, preferably having a particle size of the same order as that of the particles of active ingredients. Suitable solid diluents include sodium chloride and sodium sulphate.

Compositions of the present invention may also be in the form of a self-propelling composition wherein the active ingredient is present in solution. Such self-propelling compositions may comprise an active ingredient, propellant and co-solvent, and advantageously an antioxidant stabiliser. The propellant is one or more of those already cited above. Co-solvents are chosen for their solubility in the propellant, their ability to dissolve the active ingredient, and for their having the lowest boiling point consistent with these abovementioned properties. Suitable co-solvents are lower alkyl alcohols and ethers and mixtures thereof. The co-solvents may constitute 5 to 40% w/w of the composition, though preferably less than 20% w/w of the composition.

Antioxidant stabilisers may be incorporated in such solution-compositions to inhibit deterioration of the active ingredient and are conveniently alkali metal ascorbates or bisulfites. They are preferably present in an amount of up to 0.25% w/w of the composition.

Such self-propelling compositions may be prepared by any method known in the art. For example the active ingredient either as particles as defined hereinbefore in suspension in a suitable liquid or in up to 20% w/v solution in an acceptable co-solvent as appropriate, is mixed with any other constituents of a pharmaceutically acceptable carrier. The resulting mixture is cooled and introduced into a suitable cooled container and propellant is added thereto in liquid form; and the container is sealed.

Alternatively, such self-propelling compositions may be prepared by mixing the active ingredient either in particles as hereinbefore defined or in 2 to 20% w/v alcohol or aqueous solution as appropriate, together with the remaining constituents of the pharmaceutically acceptable carrier other than propellant; introducing the resulting mixture, optionally with some propellant, into a suitable container; sealing the container; and injecting propellant under pressure into the container at ambient temperature through a valve which comprises a part of the container and is used to control release of the composition from it. Desirably the container is purged by removing air from it at a convenient stage in the preparation of the self-propelling composition.

A suitable container for a self-propelling composition, is one provided with a manually operable valve and being constructed of aluminum, stainless steel or reinforced glass. The valve should of course be one having the desired spray characteristic, that is, the spray issuing from the valve should have the characteristics of particle size as hereinbefore defined. Advantageously the valve is of the metered type, that is a valve of the type which delivers a fixed amount of composition on the occasion of each operation of the valve, for example, about 50 or 100 microliters of composition in each delivery.

Compositions of the present invention may also be in the form of aqueous or dilute alcoholic solution, optionally a sterile solution, of the active ingredient for use in a nebuliser or atomiser, wherein an accelerated air stream is used to produce a fine mist consisting of small droplets of the solution. Such compositions usually contain a flavouring agent such as saccharin sodium and a volatile oil. A buffering agent such as sodium phosphate; an antioxidant such as sodium metabisulfite; and a surface active agent may also be included in such a composition. Desirably such a composition should contain a preservative such a methylhydroxybenzoate.

Compositions of the present invention suitable for parenteral administration conveniently comprise sterile aqueous solutions of the active ingredient, which solutions are preferably isotonic with blood of a patient under treatment. These are preferably administered intra-venously, although administration may also be effected by means of subcutaneous or intra-muscular injection. Such compositions may be conveniently prepared by dissolving solid active ingredient in water to produce an aqueous solution, and rendering said solution sterile and isotonic with human blood.

Pharmaceutical compositions of the present invention suitable for topical use include compositions suitable for administration to the skin, eyes, nose and mouth.

Compositions for use on the skin include lotions and creams comprising liquid or semi-solid emulsions, either oil-in-water or water-in-oil, which preferably contain from 0.2 to 5% w/v of the active ingredient. Ointments comprising 0.2 to 5% w/v of the active ingredient dissolved or dispersed in a semi-solid basis may also be used for topical administration to the skin. Conveniently the semi-solid basis contains liquid or semi-solid hydrocarbons, animal fat, wool alcohol or a macrogol, possibly with an emulsifying agent. Desirably the creams and ointments should contain a preservative such as methyl hydroxybenzoate.

Compositions for administration to the eye include eye drops comprising the active ingredient in aqueous or oily solution, preferably at a concentration of 0.2 to 5% w/v. Such solutions are desirably fungistatic and bacteriostatic and are preferably prepared sterile. Compositions for administration to the eye also include eye ointments which preferably comprise the same concentration of active ingredient, conveniently in the form of a salt, either dissolved in one of the ingredients of the semi-solid basis of the ointment or as a finely divided suspension therein.

Compositions suitable for administration to the nose include powder, self-propelling and spray compositions similar to those already described under compositions suitable for pulmonary administration but having when dispersed, a somewhat larger particle size of the order of 10 to 200 microns. In the case of self-propelling solution and spray compositions this effect may be achieved by choice of a valve having the desired spray characteristic i.e. being capable of producing a spray having the desired particle size or by incorporating the medicament as a suspended powder of controlled particle size. Thus the composition instead of passing into the lungs is largely retained in the nasal cavity. Other compositions suitable for nasal administration include a coarse powder having a particle size of 20 to 500 microns which is administered in the manner in which snuff is taken i.e. by rapid inhalation through the nasal passage from a container of the powder held close up to the nose. Another composition suitable for nasal administration is nasal drops comprising 0.2 to 5% w/v of the active ingredient in aqueous or oily solution.

Compositions suitable for topical administration in the mouth include lozenges comprising 10 to 100mg. of the active ingredient in a flavoured basis, usually sucrose and acacia or tragacanth; and pastilles comprising 10 to 100mg. of the active ingredient in an inert basis such as gelatin and glycerin; or sucrose and acacia.

Other therapeutic ingredients suitable for inclusion in the hereinbefore described compositions, especially in the case of those compositions intended for use in the treatment of allergic asthma, include bronchodilators. Any bronchodilator may be used in such a composition although particularly suitable bronchodilators are isoprenaline, adrenaline, orciprenaline isoethanine and physiologically acceptable acid addition salts thereof, especially isoprenaline sulphate. Conveniently the bronchodilator is present in the composition in an amount of 0.1 to 50% w/w of the weight of active ingredient present.

The present invention provides pharmaceutical compositions comprising a compound of formula I as defined hereinbefore together with a pharmaceutically acceptable carrier thereof.

Accordingly, the present invention provides a method of treatment of an allergic condition as hereinbefore defined comprising administration of a prophylactic or a therapeutic dose of a compound of formula I.

In another aspect the present invention provides a self-propelling pharmaceutical composition comprising 0.1 to 20% w/w of a compound of formula I as defined hereinbefore in the form of solid particles having a diameter of from 1 to 7µ, 0.01 to 20% w/w of surfactant and 50 to 99.9% w/w of a liquid propellant having a boiling point of below 19° C at atmospheric pressure.

In further aspects the present invention provides:

Compositions comprising a tricyclic compound of formula IV as defined hereinbefore in association with a pharmaceutically acceptable carrier therefor;

the novel tricyclic compounds of formulae V, VII and VIII as defined hereinbefore; and the novel solid tricyclic compounds of formula X, as defined hereinbefore.

In another aspect the present invention provides a method of preparing a pharmaceutical formulation suitable for use in the treatment in mammals of allergic conditions as defined hereinabove characterised in that one prepares a compound of formula I by any one of the processes described hereinabove; and optionally converts a compound of formula I so-produced to another compound of formula I; and admixes a compound of formula I so-produced with an inert carrier therefor.

The following preparations and examples illustrate the methods for preparing compounds in accordance with the present invention, as well as compounds and compositions of the present invention. In the examples and preparations, all temperatures are in degrees Celsius. Where melting points are not given for compounds of formula I, the compounds decompose at temperatures below their melting points and/or their melting points are at temperatures above those readily determinable by conventional techniques.

REFERENCE PREPARATION 1

Xanthene-2-carboxylic acid 2,4'-Dicarboxy diphenyl ether (9.4g.) was added to polyphosphoric acid (170g.) and the mixture was stirred and heated to 100° for 90 minutes, stirred at room temperature for 3 hours, and then treated with water (300 ml.). The resulting solid was filtered, washed well with water and dried in vacuo to give material mp. 298°–299°. One recrystallisation from propan-2-ol gave xanthone-2-carboxylic acid m.p. 303°–304°.

REFERENCE PREPARATION 2

Xanthone-2,7-dicarboxylic acid i. Xanthone-2,7-dicarbonitrile, prepared from 2,7-diamino-xanthone by the Sandmeyer reaction, was hydrolysed by refluxing with 60% w/w aqueous sulphuric acid (25 pts.) for 24 hours with addition of glacial acetic acid (10 pts.) to improve solubility. The solid which separated on cooling was filtered, washed with water and dried; on crystallisation from dimethyl formamide it gave xanthone-2,7-dicarboxylic acid as a white solid, m.p. ca. 420° decomp.

ii. 2,7-Dimethylxanthone (1.75g.), prepared by the method of Kobrich (Annalan, 1963,664,96), was heated in a 1:1 mixture (70 ml) of glacial acetic acid and acetic anhydride with stirring at 60°–65° C while slow addition of a warm solution of chromium trioxide (3.5g.) in a 1:1 mixture (70 ml) of acetic acid and acetic a anhydride took place. After the addition (ca 20 minutes) the mixture was stirred and heated at 70°–75° for 7 hours, then left overnight. The separated solid was washed, dried and crystallised from dimethyl formamide to give xanthone-2,7-dicarboxylic acid identical with that prepared by Method (i).

iii. The sodium salt of p-hydroxybenzonitrile (1 ml) was heated with 2,4-dicyanonitrobenzene (1 mole) in dry dimethyl sulphoxide for 18 hours at 105° to form 4-(2,4-dicyanophenoxy) benzonitrile m.p. 222°–223°, which was recovered by dilution with water, and purified by crystallisation from acetic acid. This compound was hydrolysed with 60% w/w aqueous sulphuric acid (25 pts.) mixed with glacial acetic acid (10 parts), refluxing the mixture for 24 hours; on cooling, diphenyl ether 2,4,4'-tricarboxylic acid separated. The tricarboxylic acid was cyclized either (a) by heating to 300° for 5 minutes, or (b) dissolving in concentrated sulphuric acid, heating at 100° for 3 hours and subsequently diluting with water. The solid resulting from (a) or from (b) was recrystallised from dimethyl formamide to give xanthone-2,7-dicarboxylic acid identical with that prepared by Methods (i) and (ii).

REFERENCE PREPARATION 3

Acridone - 2 - carboxylic acid

A mixture of diphenylamine-2,4'-dicarboxylic acid (4g) and concentrated sulphuric acid (40 ml.) was heated at 100° for one hour. The mixture was poured into water (700 ml.) and the solid was filtered, washed with water and dried. Recrystallisation from a mixture of dimethylformamide and ethanol gave acridone-2-carboxylic acid, m.p.: >300°.

EXAMPLE 1

9-Oxoxanthene-2,6-dicarboxylic acid

9-Oxoxanthene-2,6-dicarbonitrile, obtained from the corresponding diamine by the Sandmeyer reaction, was boiled under reflux with 60% w/w sulphuric acid (20 volumes) for 24 hours. The resulting solid was filtered off, dried, and the dissolved in warm dimethyl formamide. Ethanol was added to give 9-oxoxanthene-2,6-dicarboxylic acid which after drying had a m.p. of 440° C.

EXAMPLE 2

9-Oxoxanthene-2,6-dicarboxylic acid

A. Preparation of Diphenylether-2,5,4'-tricarbonitrile p-Hydroxybenzonitrile (2.38g.) was evaporated with normal methanolic sodium methoxide (20 ml.) to give the sodium salt of p-hydroxybenzonitrile. The sodium salt of p-hydroxybenzonitrile 2.38g.) was mixed with 2-nitroterephthalodinitrile (3.46g.) (prepared by standard procedures from 2-nitroterephthalic acid), and their solution in dimethyl sulphoxide (40 ml.) was heated for 18 hours at 110° C. Dilution of the solution with water gave diphenylether-2,5,4'-tricarbonitrile, which after crystallisation from acetic acid had m.p. 194° C.

B. Preparation of 9-oxoxanthene-2,6-dicarboxylic acid.

2,5,4'-Tricyanodiphenylether was refluxed for 24 hours with 60% sulphuric acid (20 volumes). The resulting diphenylether-2,5,4'-tricarboxylic acid was filtered off and dried. It was then dissolved in concentrated sulphuric acid (15 volumes) and left at 100° C for 2 hours. The solution was poured onto ice and gave 9-oxoxanthene-2,6-dicarboxylic acid, which was recrystallised from dimethylformamide and ethanol and then dried. The m.p. was found to be 440° C.

EXAMPLE 3

9-Oxoxanthene-2,6-dicarboxylic acid

A. Preparation of Diphenylether-2,5,4'-tricarboxylic acid.

Diphenylether-2,5,4'-tricarbonitrile (prepared as described in example 11) was refluxed with 60% w/w sulphuric acid (20 volume) and glacial acetic acid (15 volumes) for 5 hours. The resulting diphenylether-2,5,4'-tricarboxylic acid was filtered off and dried.

B. Preparation of 9-Oxoxanthene-2,6-dicarboxylic acid.

Diphenylether-2,5,4'-tricarboxylic acid was dissolved in concentrated sulphuric acid (15 volumes) and left at 100° C. for 2 hours. The reaction mixture was poured onto ice and gave 9-oxoxanthene-2,6-dicarboxylic acid which on recrystallisation from dimethylformamide and ether, and drying, had a m.p. above 400° C.

EXAMPLE 4

Xanthone-2,6-dicarboxylic acid 2,6-Dimethyl xanthone (0.9g.) (obtained according to Kobrich (Annalen, 1963, 664, p. 96)) was heated under pressure with sodium dichromate (3.6 g.) and water (55 ml.) at 240°-250° for 23 hours. The resulting mixture was filtered and the solid material was extracted thoroughly with hot water. The combined filtrates, heated to boiling and acidified with dilute hydrochloric acid, gave on slow cooling a fine precipitate of xanthone-2,6-dicarboxylic acid (synonym: 9-oxoxanthene-2,6-dicarboxylic acid.) m.p. >400°.

EXAMPLE 5

Disodium-9-oxoxanthene-2,6-dicarboxylate

9-Oxoxanthene-2,6-dicarboxylic acid was dissolved in dimethyl formamide and neutralized with a Normal solution of sodium methoxide in methanol (2 equivalents). On the addition of further methanol a precipitate of disodium-9-oxoxanthene-2,6-dicarboxylate was obtained. This crystallised with 3 molecules of water of crystallisation per molecule of disodium-9-oxoxanthene-2,6-dicarboxylate and was soluble in water.

EXAMPLE 6

Diethyl xanthone-2,6-dicarboxylate

Xanthone-2,6-dicarboxylic acid was refluxed in ethanol (50 volumes) containing concentrated sulphuric acid (10 volumes) for 3 days. The solution was then poured on to ice and made just alkaline with sodium carbonate. Diethyl xanthone-2,6-dicarboxylate thus obtained was filtered off. After crystallisation from aqueous ethanol it melted at 156°-158°.

EXAMPLE 7

Methyl xanthone-2-carboxylate

Xanthone-2-carboxylic acid (12 g.) was treated with dry methanol (30 ml.) and sulphuric acid (2.5 ml.) and the mixture was heated to reflux for 20 hours, and then most of the methanol was removed under reduced pressure. The residue was partitioned between water and dichloromethane, the organic layer washed with water and with aqueous sodium bicarbonate, dried over anhydrous sodium sulphate and evaporated under reduced pressure. The residual solid was recrystallised from benzene to give methyl xanthone-2-carboxylate m.p. 209°-210°.

EXAMPLE 8

Xanthone-1,7-dicarboxylic acid.

Xanthone-1,7-dicarbonitrile prepared from 1,7-diamino-xanthone by the Sandmeyer reaction, was hydrolysed by refluxing for 24 hours with a mixture of 60% aqueous sulphuric acid (25 parts) and glacial acetic acid (10 parts). The solid which separated on cooling, crystallised from dimethyl sulphoxide on addition of ethanol to give xanthone-1,7-dicarboxylic acid, m.p. 355°-360°.

EXAMPLE 9

Acridone-2,6-dicarboxylic acid 2,6-Dimethylacridone, prepared by the cyclization of 4',5-dimethyldiphenylamine-2-carboxylic acid, was heated at 200°-250° with an aqueous solution of sodium dichromate dihydrate (3 moles) in an autoclave for 17 hours. After cooling overnight the contents of the autoclave were washed with hot water into a beaker, filtered hot, and the residual chromium oxide washed thoroughly with hot water. The alkaline filtrate and washings were combined, evaporated to a small volume and acidified with concentrated hydrochloric acid. The mixture was centrifuged to recover the fine precipitate and the resulting cake of solid was dried and disolved in dimethyl sulphoxide. On addition of ethanol to the filtered solution, acridone-2,6-dicarboxylic acid was obtained as an orange solid which decomposed above 460°.

EXAMPLE 10

10-Methylacridone-2,7-dicarboxylic acid.

10-Methylacridone-2,7-dicarbonitrile, prepared from 2,7-diamino-N-methylacridone by the Sandmeyer reaction, was heated under reflux at 190° with 60% w/w aqueous sulphuric acid (25 parts) with mechanical stirring for 24 hours. The yellow solid which separated on cooling was filtered, washed, dried, and crystallised from dimethyl sulphoxide with addition of ethanol to give 10-methylacridone-2,7-dicarboxylic acid, which decomposed at 465° after sintering at 450°.

EXAMPLE 11

Acridone-2,6-dicarboxylic acid dipotassium salt

To a solution of acridone-2,6-dicarboxylic acid in warm dimethyl sulphoxide (20 volumes) was added N solution of potassium hydroxide in methanol (2 equivalents). The mixture was diluted with methanol (30 volumes) and the precipitate of acridone-2,6-dicarboxylic acid dipotassium salt was filtered off and dried. The salt dissolved in water to give a yellow solution showing a blue fluorescence.

EXAMPLE 12

10-Methylacridone-2,7-dicarboxylic acid dipotassium salt

10-Methylacridone-2,7-dicarboxylic acid dipotassium salt was prepared by a process similar to that described in Example 11.

EXAMPLE 13

Dimethylacridone-2,6-dicarboxylate

Acridone-2,6-dicarboxylic acid was refluxed with thionyl chloride (15 volumes) and dimethyl formamide (5 volumes) until the solution was clear. Excess of solvent was removed under reduced pressure and the resulting residue was carefully treated with methanol. A solution was obtained from which crystallised dimethyl acridone-2,6-dicarboxylate crystallised as an orange solid, m.p. 420°, and containing 0.5 mole of water.

EXAMPLE 14

Acridone-2,6-dicarboxamide

Acridone-2,6-dicarboxylic acid was refluxed with thionyl chloride (15 volumes) and dimethyl formamide (5 volumes) until the solution was clear. Excess soluent was removed under reduced pressure. Excess aqueous ammonia (d 0.880) was added and the resulting mixture evaporated under reduced pressure to remove the excess of ammonia. A crystalline precipitate of acridone-2,6-dicarboxamide was formed, which, after filtration and drying, formed a yellow powder which sublimed, but did not melt, at temperatures up to 400° C.

EXAMPLE 15

Xanthone-2,6-dicarboxamide

Xanthone-2,6-dicarboxylic acid was refluxed with an excess of thionyl chloride containing one-third of its volume of dimethyl formamide, until the solution was clear. Excess of solvent was removed under reduced pressure and the residue carefully treated with aqueous ammonia (d 0.880). The resulting precipitate was filtered and crystallised from dimethyl formamide:ethanol to give xanthone-2,6-dicarboxamide, m.p. 383°-384°, which sublimed readily.

EXAMPLE 16

Dimethylxanthone-2,6-dicarboxylate

Xanthone-2,6-dicarboxylic was treated with thionyl chloride and dimethyl formamide by a process as described in example 15. After removal of excess soluent, the residue was carefully treated with methanol. A crystalline material was obtained which, on recrystallisation from ethanol, gave colourless laminae of dimethyl xanthone-2,6-dicarboxylate, m.p. 214°-215° C.

EXAMPLE 17

Preparation of Xanthone-2,5-dicarboxylic acid

4-Cyanophenol (11.9 g.) was treated with excess concentrated aqueous sodium hydroxide. To the resulting sodium - 4 - cyanophenoxide was added 2,6-dicyanonitrobenzene (17.3g.) dissolved in dimethyl sulphoxide. The solution was maintained at 110° for 19 hours and then poured into water. The 2,6,4'-tricyano-diphenylether thus obtained was filtered off, dried and heated under reflux in glacial acetic acid (110 mls.) with 60% w/v aqueous sulphuric acid (180 ml.) for 6 hours. On cooling the reaction mixture, diphenylether-2,6,4'-tricarboxylic acid separated out as a crystalline solid which was filtered off, dried and heated in concentrated sulphuric acid at 100° C for 1 hour. Ice was then added to the mixture to yield xanthone-2,5-dicarboxylic acid which was crystallised from dimethyl formamide solution on addition of aqueous ethanol. The crystals sublimed but did not melt up to 330° C.

EXAMPLE 18

Preparation of 6-Nitroacridone-2-carboxylic acid

2-Chloro-4-nitrobenzoic acid (10.1 g.) and 4-aminobenzoic acid (6.85 g.) were mixed and treated with aqueous potassium carbonate [13.8 g. of solid] to produce a solution of the mixed potassium salts. The mixture of salts was obtained in the solid state by evaporation and drying; it was suspended in dry dimethyl formamide (100 ml.) together with amhydrous potassium carbonate (6.9 g.) copper powder (0.25 g.) and cuprous chloride (0.25 g.). The mixture was stirred and heated at 170°-180° C for 4½ hours, then diluted with water to 600 ml., warmed to 60° C, filtered, cooled and acidified. The resulting 5-nitrodiphenylamine-2,4'-dicarboxylic acid gave crystals of a monohydrate, m.p. 285°-287°, from methanol. This was heated at 110°-120° for 5 hours with an excess of polyphosphoric acid. Addition of the hot syrup to hot water yielded a precipitate of 6-nitro-acridone-2-carboxylic acid, which, from dimethylformamide, gave crystals which lost solvent at 150°–160°/0.5 mm., but which did not melt up to 450°. The acid dissolved in dilute alkalis such as 1% aqueous ethanolamine.

EXAMPLE 19

Preparation of 6-Chloroacridone-2-carboxylic acid 2,4-Dichlorobenzoic acid (19.1 g.) and 4-aminobenzoic acid (13.7 g.) were independently treated with aqueous potassium carbonate 6.9 g. of solid in each instance). The potassium salts obtained by evaporation were thoroughly dried out and mixed in pentyl alcohol (100 ml.). To the alcoholic suspension was added anhydrous potassium carbonate (13.5 g.), copper powder (0.5 g.) and cuprous chloride (0.5 g.) and the mixture was stirred under gentle reflux at 165°–175° C. After 2 hours a further amount of pentyl alcohol (100 ml.) was added, and the mixture was heated for 3 hours more. Excess solvent was then removed by steam-distillation and the resultant aqueous alkaline solution was filtered through charcoal and acidified to give a heavy precipitate. This was filtered off, dried and crystallised from ethanol and the pure 5-chlorodiphenylamine-2,4-dicarboxylic acid thus obtained was heated in an excess of tetraphosphoric acid at 120° C for 4½ hours with stirring. Addition of the hot syrup to hot water gave a precipitate of 6-chloroacridone-2-carboxylic acid. This was almost insoluble in most organic solvents but separated from dimethyl sulphoxide in crystals containing one third of a molecule of solvent and which sublimed above 450° C but did not melt. The acid dissolved readily in dilute alkalis much as 1% w/v aqueous ethanolamine.

EXAMPLE A

Nasal Drops

| | |
|---|---|
| Disodium xanthone-2,6-dicarboxylate | 0.5 g |
| Chlorbutol | 0.5 g |
| Sodium Chloride | 0.5 g |
| Distilled Water | to 100.0 ml |

The ingredients were dissolved together in Distilled Water (95ml) at room temperature. The solution was made up to volume with the balance of the Distilled Water and clarified by passage through a filter of sintered glass, porosity No. 4.

EXAMPLE B

Nasal Drops

| | |
|---|---|
| Xanthone-2,6-dicarboxylic acid (micronised powder) | 0.5 g |
| Hypromellose 50 | 0.6 g |
| Chlorbutol | 0.5 g |
| Sodium Chloride | 0.5 g |
| Distilled Water | to 100.0 ml |

Chlorbutol was dissolved in Distilled Water (30 ml) at 75° C. Hypromellose was added and dispersed. An ice-cold solution of Sodium Chloride in Distilled Water (60 ml.) was added, and the mixture stirred until Hypromellose dissolved completely. The Acid was added and thoroughly dispersed, and the mixture diluted to volume.

EXAMPLE C

Eye Drops

| | |
|---|---|
| Disodium xanthone-2,6-dicarboxylate | 0.20 g |
| Sodium Chloride | 0.83 g |
| Methyl Hydroxybenzoate | 0.06 g |
| Propyl Hydroxybenzoate | 0.04 g |
| Distilled Water | to 100.00 ml |

Methyl and Propyl Hydroxybenzoate were dissolved in Distilled Water (70 ml) at 75° C. Sodium Chloride was added and dissolved and the solution allowed to cool. Disodium salt was added and dissolved, and the final solution made up to volume and sterilised by filtration.

EXAMPLE D

Capsules of Powder.

| | |
|---|---|
| Disodium xanthone-2,6-dicarboxylate (0.5 to 7.0µ powder) | 4.0 mg |
| Lactose (30–90µ powder) | 46.0 mg |

The Powders were mixed until homogenous and filled in suitable sized hard gelatin capsules, 50 mg per capsule, for use in a powder inhalation device, such as the type described in U.K. Pat. No. 1,182,779.

EXAMPLE E

Lotion for Topical Use.

| | |
|---|---|
| Disodium xanthone-2,6-dicarboxylate | 1.5 g |
| Sorbitan Monolaurate | 0.6 g |
| Polysorbate 20 | 0.6 g |
| Cetostearyl Alcohol | 1.2 g |
| Glycerin | 6.0 g |
| Methyl Hydroxybenzoate | to 0.2 g |

To a solution of Methyl Hydroxybenzoate and Glycerin in Distilled Water (70 ml) at 75° C was added a mixture of Sorbitan Monolaurate, Polysorbate 20 and Cetostearyl Alcohol at the same temperature. The resulting emulsion was homogenised using high speed stirring and allowed to cool. A solution of the Disodium salt in the remaining Distilled Water was added and the whole stirred.

EXAMPLE F

Injection Solution

| | |
|---|---|
| Disodium xanthone-2,6-dicarboxylate | 10.0 mg |
| Water for Injection | to 1.0 ml |

The Disodium Salt was dissolved in half the Water for Injection. The remaining Distilled Water was added and the solution sterilised by filtration. The sterile solution was filled into an ampoule under aseptic conditions.

EXAMPLE G

Aerosol Powder

| | |
|---|---|
| Disodium xanthone-2,6-dicarboxylate | 400 mg |
| Sorbitan Trioleate | 200 mg |
| Trichlorofluoromethane | 4.5 g |
| Dichlorodifluoromethane | to 10.0 ml |

Sorbitan Trioleate was dissolved in Trichlorofluoromethane. Disodium salt was added and thoroughly dispersed. The mixture was transferred to a suitable aerosol canister and Dichlorodifluoromethane injected through the valve system. The composition provides 4 mg of Disodium salt in each 100μl dose.

EXAMPLE H

Aerosol Powder

| | |
|---|---|
| Xanthone-2,6-dicarboxylic acid | 500 mg |
| Sorbitan Trioleate | 100 mg |
| Saccharin (6–10μ powder) | 5 mg |
| Menthol | 2 mg |
| Sodium Sulphate (2–6μ powder) | 50 mg |
| Trichlorofluoromethane | to 4.5 g |
| Dichlorodifluoromethane | to 10.0 ml |

Sorbitan Trioleate and Menthol were dissolved in Trichlorofluoromethane Acid, Saccharin and Sodium Sulphate were added and dispersed. The suspension was transferred to a suitable aerosol canister. Dichlorodifluoromethane was injected through the valve system. The composition provides 5 mg of Acid in each 100 μl dose.

EXAMPLE I

Lozenge

| | |
|---|---|
| Disodium xanthone-2,6-dicarboxylate | 50 mg |
| Mannitol | 400 mg |
| Dextrose Monohydrate | 400 mg |
| Magnesium Stearate | 20 mg |
| Granulated with a solution of Polyvinylpyrrolidone; 5% in 25% Alcohol. | |

A mixture of Disodium Salt, Mannitol and Dextrose Monohydrate was granulated with Polyvinylpyrrolidone in Alcohol, and the granule dried. Magnesium Stearate was sifted on and the mixture compressed to produce lozenges of the desired shape.

EXAMPLE J

Aerosol Powder

| | |
|---|---|
| Diethyl xanthone-2,6-dicarboxylate | 250 mg |
| Ethyl Alcohol | 4 g |
| Saccharin | 1 mg |
| Dichlorodifluoromethane | to 10 ml |

The saccharin and the diethyl ester were dissolved in the ethyl alcohol. The resulting solution was transferred to a suitable aerosol canister and dichlorodifluoromethane injected through the valve system. The composition provides 2.5 mg of diethyl ester in each 100μl dose.

EXAMPLE K

Pharmaceutical Compositions

Pharmaceutical compositions were prepared in similar manner to those described hereinabove but with different active ingredients as follows:

i. Pharmaceutical compositions wherein the active ingredient comprised acridone-2,6-dicarboxylic acid, were prepared in similar manner to those described in Examples C and I;

ii. Pharmaceutical compositions wherein the active ingredient comprised disodium acridone-2,6-dicarboxylate were prepared in similar manner to those described in Examples A, B, D, E, F, G, H and J; and iii. Pharmaceutical compositions wherein the active ingredient comprised diethylacridone-2,6-dicarboxylate were prepared in similar manner to those described in Examples C and I.

I claim:

1. A method of inhibiting the symptoms of asthma or allergic rhinitis in a mammal susceptible to asthma or allergic rhinitis, which comprises administration to said mammal of a prophylactically effective anti-asthma or anti-allergic rhinitis non toxic dose of a compound of formula (I)

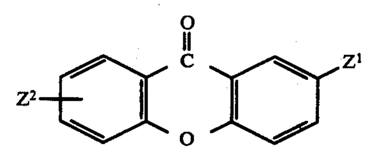

(I)

wherein $Z^1$ is carboxyl, a pharmaceutically acceptable carboxylate salt, alkyl carboxylate, carboxamide, N-alkyl carboxamide or N,N-dialkylcarboxamide, and $Z^2$ is a substituent in the 6-position selected from the meanings of $Z^1$ as defined, wherein the "alkyl" moiety of alkyl carboxylate, N-alkylcarboxamide and N,N-dialkyl carboxamide has 1 to 6 carbon atoms.

2. A method as claimed in claim 1 wherein in formula I $Z^1$ and $Z^2$ are each selected from carboxyl, a pharmaceutically acceptable carboxylate salt, alkyl carboxylate or carboxamide.

3. A method as claimed in claim 2 wherein the pharmaceutically acceptable salt is selected from the group consisting of sodium, potassium, magnesium, calcium, ammonium and a salt with an organic base.

4. A method as claimed in claim 2 wherein the compound of formula I is xanthone-2,6-dicarboxamide, dimethyl xanthone-2,6-dicarboxylate or diethyl xanthone-2,6-dicarboxylate.

5. A method as claimed in claim 1 wherein the compound of formula I is xanthone-2,6-dicarboxylic acid or a pharmaceutically acceptable salt thereof.

6. A method as claimed in claim 1 wherein the compound of formula I is xanthone-2,6-dicarboxylic acid.

7. A method as claimed in claim 1 wherein the compound of formula I is disodium xanthone-2,6-dicarboxylate.

8. A method according to claim 1 wherein pulmonary administration is employed.

9. A method according to claim 1 wherein the tricyclic compound is administered in the form of a powder having a particle size in the range from 0.5 to 7μ.

10. A method according to claim 1 wherein the dose is from 2μg. to 100 mg. per kg. bodyweight of the mammal.

11. A method according to claim 1 wherein the dose is from 30 μg to 0.3 mg. per kg. bodyweight of the mammal undergoing treatment.

12. A method of preventing the symptoms of allergic asthma in a human comprising pulmonary administration to the human of from 30 μg to 0.3 mg, per kg. bodyweight of said human, of disodium xanthone-2,6-dicarboxylate, in the form of a powder having a particle size in the range from 0.5 to 7μ.

13. A method for the prevention of the symptoms of hayfever in a human comprising administration to the human of from 2 μg. to 6 mg. per kg. bodyweight of said human, of disodium xanthone-2,6-dicarboxylate.

14. A method according to claim 1 wherein the tricyclic compound is administered in association with an effective bronchodilating dose of a bronchodilator.

15. A method according to claim 14 wherein the dose of the bronchodilator is from 0.1 to 100% w/w of the dose of the tricyclic compound.

16. A method for the prophylaxis of allergic asthma in a human, comprising pulmonary administration to said human of a prophylactically effective anti-allergic dose of disodium xanthone-2,6-dicarboxylate in association with an effective bronchodilating dose of a bronchodilator.

17. A method according to claim 16 wherein the dose of disodium xanthone-2,6-dicarboxylate is from 30μg. to 0.3 mg. and the dose of bronchodilator is from 0.3μg to 0.3mg.

18. A method for prophylaxis of allergic rhinitis or asthma of a mammal comprising pulmonary administration to the mammal of a prophylactically effective anti-allergic dose of disodium xanthone-2,6-dicarboxylate in the form of a powder having a particle size in the range of 0.5 to 7 μ.

19. A method for the prophylaxis of allergic rhinitis, asthma, urticaria, eczema or conjunctivitis of a mammal comprising administration to the mammal of a prophylactically effective anti-allergic dose of a tricyclic compound of formula

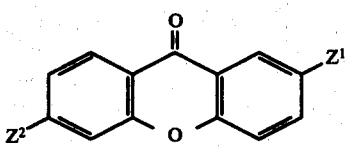

wherein $Z^1$ is a pharmaceutically acceptable carboxylate salt selected from the group consisting of a carboxylate salt with a potassium sodium, calcium, magnesium, ammonium, and organic base cation and $Z^2$ is selected from the group consisting of $Z^1$ as defined herein, carboxyl, alkyl carboxylate having 1 to 6 carbon atoms in the 'alkyl' moiety, carboxamide and carboxamide N-substituted by alkyl having 1 to 6 carbon atoms.

20. A composition for the prophylaxis of an allergic condition selected from the group consisting of allergic rhinitis, asthma, urticaria, conjunctivitis and eczema of a mammal comprising a prophylactically effective non-toxic antiallergic amount of a tricyclic compound of formula

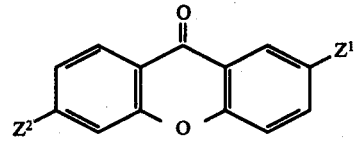

wherein $Z^1$ is a pharmaceutically acceptable carboxylate salt group selected from the group consisting of a carboxylate salt with a potassium, sodium, calcium, magnesium, ammonium and organic base cation and $Z^2$ is selected from the group consisting of $Z^1$ as defined herein, carboxyl alkyl carboxylate having 1 to 6 carbon atoms in the 'alkyl' moiety, carboxamide and carboxamide N-substituted by alkyl having 1 to 6 carbon atoms, and a pharmaceutically acceptable salt carrier therefore.

21. A composition as claimed in claim 20 wherein the tricyclic compound is in the form of solid particles having a diameter of from 0.5 to 7μ.

22. A pharmaceutical composition for pulmonary administration to a mammal for inhibiting the symptoms of asthma or allergic rhinitis comprising an asthma or allergic rhinitis symptom inhibition effective non-toxic amount of disodium xanthone-2,6-dicarboxylate in the form of solid particles having a diameter of from 0.5 to 7μ and a pharmaceutically acceptable carrier therefore.

23. A composition as claimed in claim 22 which is in the form of a self-propelling aerosol for pulmonary administration.

24. A composition for the prophylaxis of an allergic condition selected from the group consisting of allergic rhinitis, asthma, urticaria, conjunctivitis and eczema of a mammal comprising a prophylactically effective non-toxic anti-allergic amount of xanthone-2,6-dicarboxylic acid or a pharmaceutically acceptable salt thereof in association with a pharmaceutically acceptable carrier therefor.

* * * * *